United States Patent [19]
Grant

[11] Patent Number: 5,477,863
[45] Date of Patent: Dec. 26, 1995

[54] COLLECTION KIT WITH A SAMPLE COLLECTOR

[76] Inventor: Michael A. Grant, 2708 "S" St., Vancouver, Wash. 98663

[21] Appl. No.: 47,746

[22] Filed: Apr. 14, 1993

[51] Int. Cl.⁶ ................................................. A61B 10/00
[52] U.S. Cl. ................................................. 128/759
[58] Field of Search .................... 128/749, 757, 128/759; 604/1, 2

[56] References Cited

U.S. PATENT DOCUMENTS

| | | | |
|---|---|---|---|
| 3,512,518 | 5/1970 | Mishkin et al. | 128/759 |
| 4,707,450 | 11/1987 | Nason | 128/759 |
| 4,788,985 | 12/1988 | Manning et al. | 128/759 |
| 4,803,998 | 2/1989 | Kezes et al. | 128/759 |
| 5,063,026 | 11/1991 | Wong | 128/759 |
| 5,084,005 | 1/1992 | Kachigian | 128/759 |

Primary Examiner—Max Hindenburg
Attorney, Agent, or Firm—W. Edward Johansen

[57] ABSTRACT

A collection kit includes a sample container with a cap and a sample collector. The sample collector includes a holder, a swab and a plunger. The holder is formed out of a tube which has a first end with a slot and a second end. The swab is formed out of a collection material with a first side-edge and a second side-edge. The swab is coupled to the slot of the holder adjacent to the first side-edge. The swab has a plurality of notches cut along the second side-edge. The holder draws the swab along a tissue surface in order to collect either cells or fluids for investigation. Once the sample collector has collected a tissue sample, the plunger is slidably inserted into the holder so that the plunger dislodges the swab from the slot in the holder in order for the swab to be deposited into the sample container.

2 Claims, 1 Drawing Sheet

U.S. Patent
Dec. 26, 1995
5,477,863
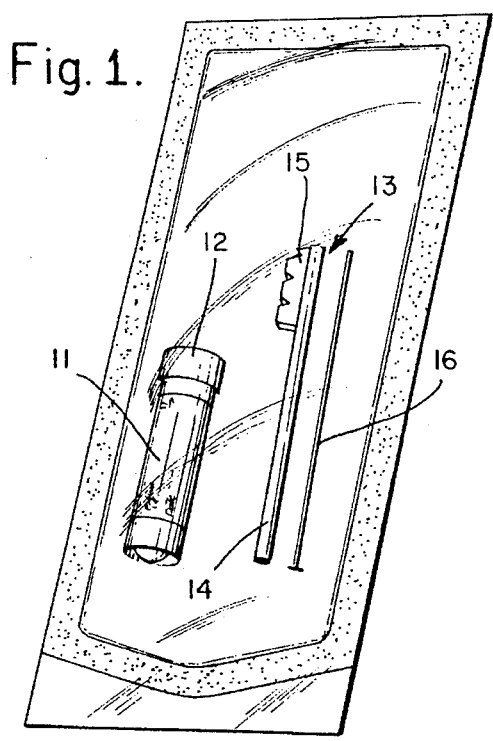
Fig. 1.
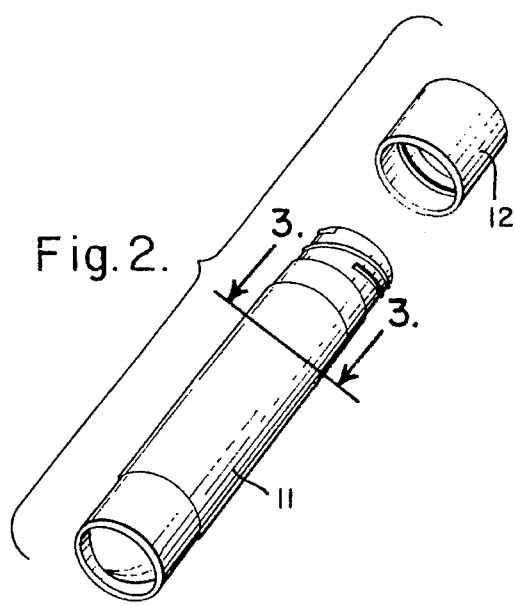
Fig. 2.
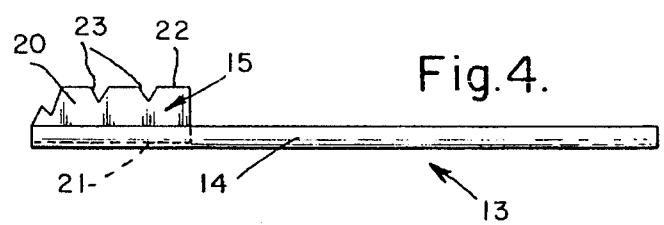
Fig. 4.
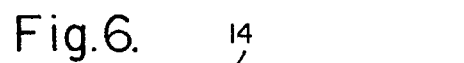
Fig. 5.
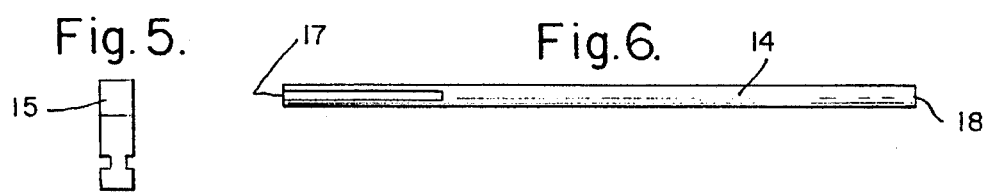
Fig. 6.
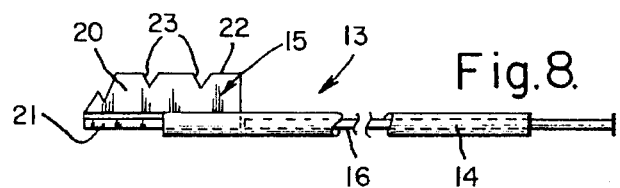
Fig. 8.
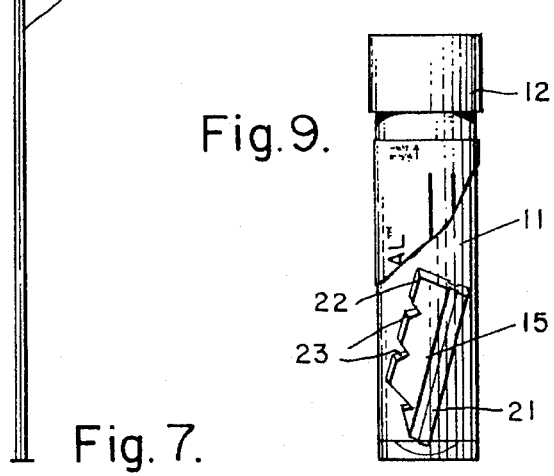
Fig. 9.
Fig. 7.
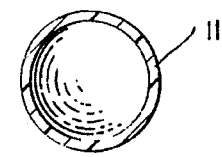
Fig. 3.

COLLECTION KIT WITH A SAMPLE COLLECTOR

BACKGROUND OF THE INVENTION

The field of the invention is sample collectors and collection kits including sample collectors and sample containers.

U.S. Pat. No. 5,133,361 teaches a biopsy brush for abrading and recovering samples of tissue to be investigated includes a plurality of abrading elements, spacers and a flexible strand. The abrading elements are individually and separately spindled onto the strand. Each abrading element has an abrading periphery. The spacers space these abrading peripheries apart from one another. The flexibility of the flexible strand where the abrading elements are located enables the individual abrading elements in the group of abrading elements separately to deflect in response to change in the shape of the tissue being abraded.

U.S. Pat. No. 5,084,005 teaches a swab for collection of biological samples which includes a handle having a proximal end and a distal end and a swabbing tip. The swabbing tip is formed of closed cell polymeric foam and is disposed at the distal end for contacting and collecting biological samples.

U.S. Pat. No. 4,963,325 teaches a disposable, pre-packaged devices which includes an elongated holder member, a swab, another holder member and a capture media element assemblage. The device is particularly suitable for conducting diagnostic procedures based on immunological reactions using specimens gathered in the absorbent tip of a swab. The elongated holder member includes a structure for supporting and positioning the swab. The capture media element assemblage as suitable for conducting an immunoassay test. The other holder member is hingedly mounted at one end of the elongated holder member and carries the capture media element assemblage.

U.S. Pat. No. 4,707,450 teaches a specimen collection unit which has a fibrous swab tip at one end of an elongated hollow shank for use in collecting a biological specimen. The shank is carried by an elongated base of a resilient plastic material and containing one or more reagents which can be pumped through the shank to the swab tip by applying manual pressure to the base. An elongated cap removably fits onto the base over the shank and the swab tip, with the cap including an additional reagent and a well into which the additional reagent can be delivered for contacting the swab tip.

U.S. Pat. No. 4,720,017 teaches a specimen kit which includes a swab tip and a shaft. Use of the specimen kit reduces significantly the possibility of contamination of the specimen by either user or container, contamination of the patient by the swab used to obtain the specimen and contamination of a subsequent handler of the container by the specimen. The specimen kit permits the collected specimen to be transported to the diagnostic processing laboratory in common, widely used medical specimen mailing containers, while permitting the use of swab lengths that are appropriate to the type of specimen desired. A unique double-ended stopper maintains the specimen container sterile until use, then acts as a cap for engaging the shaft for withdrawal while maintaining a tight and sterile shipping container after the specimen is taken and while it is subsequently handled.

U.S. Pat. No. 4,749,655 teaches a self-contained specimen collecting which has all of the advantages of the known specimen collecting units and which is characterized by the ability to preserve microorganisms during the transporting thereof in the transporting unit. The specimen collecting unit has a pledget composed of carbon fiber. The use of a carbon fiber pledget has been found to have a synergistic effect in preserving the viability of microorganisms which are obtained by use of the swab of the specimen collecting and transporting unit.

U.S. Pat. No. 4,813,432 teaches a swab transport apparatus which stores and transports to a laboratory a swab containing a specimen such as a microorganism. The uncontaminated swab is pre-packaged within a sterile swab storage chamber of the apparatus from which it can conveniently be removed for taking a sample.

SUMMARY OF INVENTION

The present invention is generally directed to a sample collector including a holder and a swab. The holder draws the swab along a tissue surface in order to collect either cells or fluids for investigation.

In a first separate aspect of the present invention, the holder has a first end with a slot and a second end. The swab is formed out of a collection material with a first side-edge and a second side-edge. The swab is coupled to the slot of the holder adjacent to the first side-edge.

In a second separate aspect of the present invention the swab has a plurality of notches cut along the second side-edge.

In a third separate aspect of the present invention, the holder is formed out of a tube. The sample collector also includes a plunger which is slidably inserted into the holder at the second thereof. The plunger dislodges the swab from the slot in the holder.

In a fourth separate aspect of the present invention, the sample collector is used in combination with a sample container having a cap to form a collection kit. When the plunger dislodges the swab from the slot in the holder, the swab may be deposited into the sample container.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

BRIEF DESCRIPTION THE DRAWING

FIG. 1 is a top plan of a collection kit including a package, a sample container with a cap and a sample collector including holder, a swab and a plunger according to the present invention.

FIG. 2 is a perspective drawing of the sample container of FIG. 1 with the cap having been removed apart therefrom.

FIG. 3 is a cross-sectional of the sample container of FIG. 1 taken along 3—3 of FIG. 2.

FIG. 4 is a side elevational view of the sample collector of FIG. 1.

FIG. 5 is a front elevational view of the swab of the sample collector of FIG. 1.

FIG. 6 is a top plan view of the holder of the sample collector of FIG. 1.

FIG. 7 is a side elevational view of the plunger of FIG. 1.

FIG. 8 is a partial side elevational view of the sample collector of FIG. 1 with the plunger being inserted into the holder in order to remove the swab.

FIG. 9 is a side elevational view of the sample container of FIG. 1 with the swab of the sample collector of FIG. 1 being disposed therein and the cap enclosing the sample container.

DESCRIPTION OF THE PREFERRED EMBODIMENT

Referring to FIG. 1 in conjunction with FIG. 2 and FIG. 3 a collection kit 10 includes a sample container 11 with a cap 12 and a sample collector 13. The sample container 11 may contain a buffering solution. The sample collector 13 includes a holder 14, a swab 15 and plunger 16.

Referring to FIG. 4 in conjunction with FIG. 5 and FIG. 6 the holder 14 is formed out of a tube which has a first end 17 with a slot 18 and a second end 19. The swab 15 is formed out of a collection material 20 with a first side-edge 21 and a second side-edge 22. The swab 15 is coupled to the slot 18 of the holder 14 adjacent to the first side-edge 23. The swab has a plurality of notches 23 cut along the second side-edge 22. The holder 14 draws the swab 15 along a tissue surface in order to collect either cells or fluids for investigation.

Referring to FIG. 7 in conjunction with FIG. 8 and FIG. 9 once the sample collector 13 has a collected a tissue sample the plunger 16 is slidably inserted into the holder 14 so that the plunger 16 dislodges the swab 15 from the slot 18 in the holder 14 in order for the swab 15 to be deposited into the sample container 11.

From the foregoing it can be seen that a collection kit including a sample container with a cap and a sample collector having a holder, a swab and a plunger has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:

1. A collection kit comprising:
  a. a sample container with a cap;
  b. a holder formed out of a tube having a first end with a slot and a second end;
  c. a swab formed out of a collection material with a first side-edge and a second side-edge and having a plurality of notches cut along said second side-edge and coupled to said slot of said holder adjacent to said first side-edge whereby said holder draws said swab along a tissue surface in order to remove cells for investigation; and
  d. a plunger which is slidably inserted into said holder whereby said plunger dislodges said swab from said slot in said holder so that said swab may be deposited into said sample container.

2. A sample collector comprising:
  a. a holder formed out of a tube having a first end with a slot and a second end;
  b. a swab formed out of a piece of collection material with a first side-edge and a second side-edge and coupled to said slot of said holder adjacent to said first side-edge whereby said holder draws said swab along a tissue surface in order to collect either cells or fluids for investigation; and
  c. a plunger which may be slidably inserted into said holder so that said plunger dislodges said swab from said slot in said holder.

* * * * *